United States Patent [19]

Chatterjee et al.

[11] 4,105,033

[45] Aug. 8, 1978

[54] POWDERED GRAFTED CELLULOSE

[75] Inventors: Pronoy Kumar Chatterjee, Spotswood; Graham Kenneth Morbey, Belle Mead, both of N.J.

[73] Assignee: Personal Products Company, Milltown, N.J.

[21] Appl. No.: 781,916

[22] Filed: Mar. 28, 1977

Related U.S. Application Data

[63] Continuation-in-part of Ser. No. 531,149, Dec. 9, 1974, abandoned.

[51] Int. Cl.² ............................................. A61F 13/20
[52] U.S. Cl. ................................. 128/285; 128/296; 162/146; 162/149; 162/176; 162/177; 260/17.4 R; 260/17.4 GC; 260/17.4 CL; 428/283; 428/306; 428/326; 428/372; 428/536; 428/913
[58] Field of Search .............. 428/283, 284, 326, 535, 428/536, 913, 393, 402, 372, 240, 243, 281, 306, 534; 260/17.4 GC, 17.4 R, 17.4 CL; 128/296, 290 P, 285, 284; 162/149, 146, 176, 177

[56] References Cited

U.S. PATENT DOCUMENTS

| | | | |
|---|---|---|---|
| 3,381,688 | 5/1968 | Satas | 128/296 |
| 3,528,421 | 9/1970 | Vaillancourt | 128/296 |
| 3,597,306 | 8/1971 | Mesek | 428/283 |
| 3,868,955 | 3/1975 | Steiger et al. | 128/296 |
| 3,888,256 | 6/1975 | Studinger | 128/296 |
| 3,889,678 | 6/1975 | Chatterjee et al. | 260/17.4 CL |

Primary Examiner—George F. Lesmes
Assistant Examiner—Stanley S. Silverman
Attorney, Agent, or Firm—Jason Lipow

[57] ABSTRACT

A selected powdery form of a graft copolymer containing hydrophilic chains provides a highly moisture-absorbent media which is suitable for use in absorbent bodies, particularly those used for absorbing body exudates such as catamenial devices, diapers, wound dressings, surgical sponges, incontinence pads and the like. The powdered form of said copolymers is useful alone or in combination with other absorbent materials in making up the absorbent bodies.

13 Claims, 9 Drawing Figures

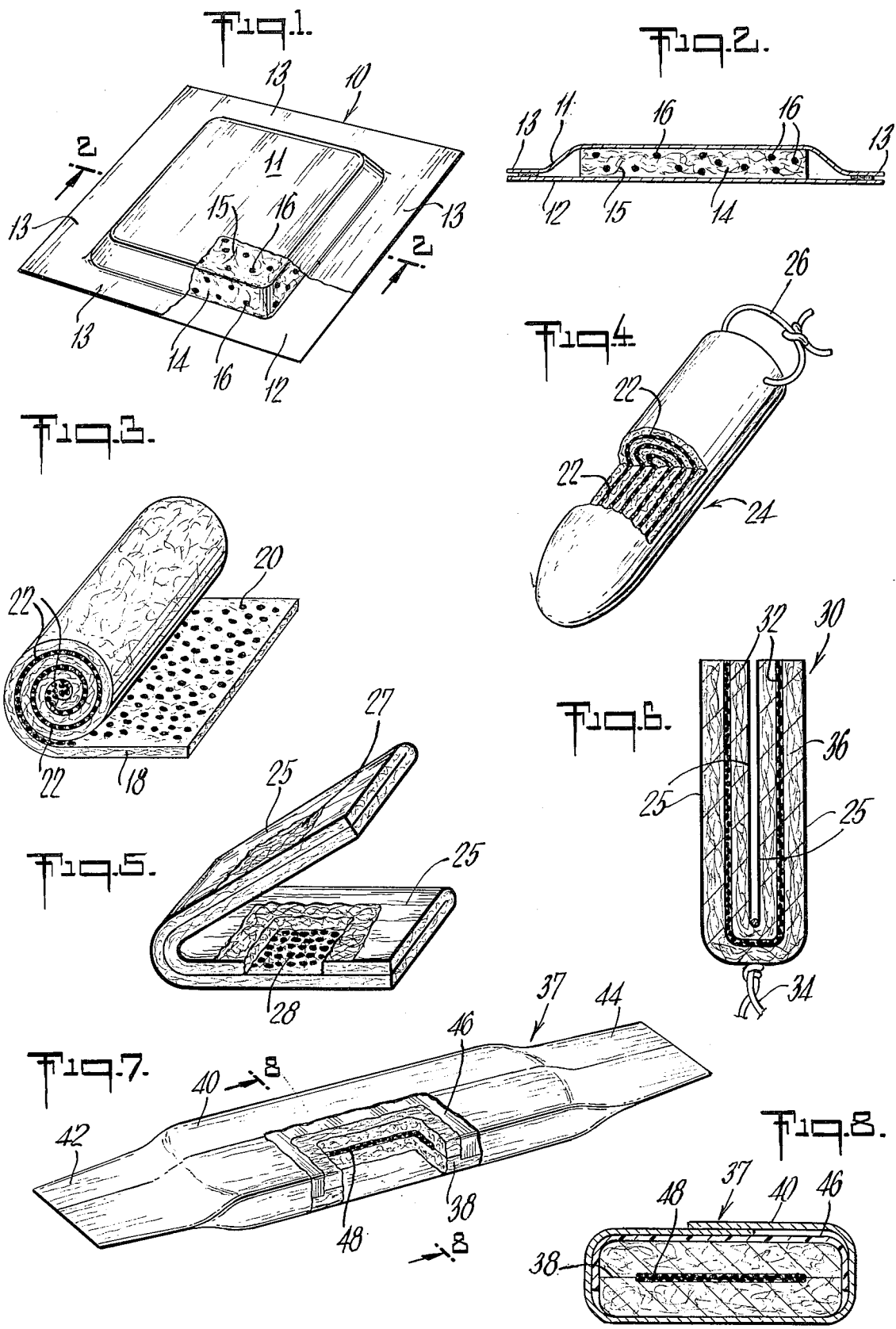

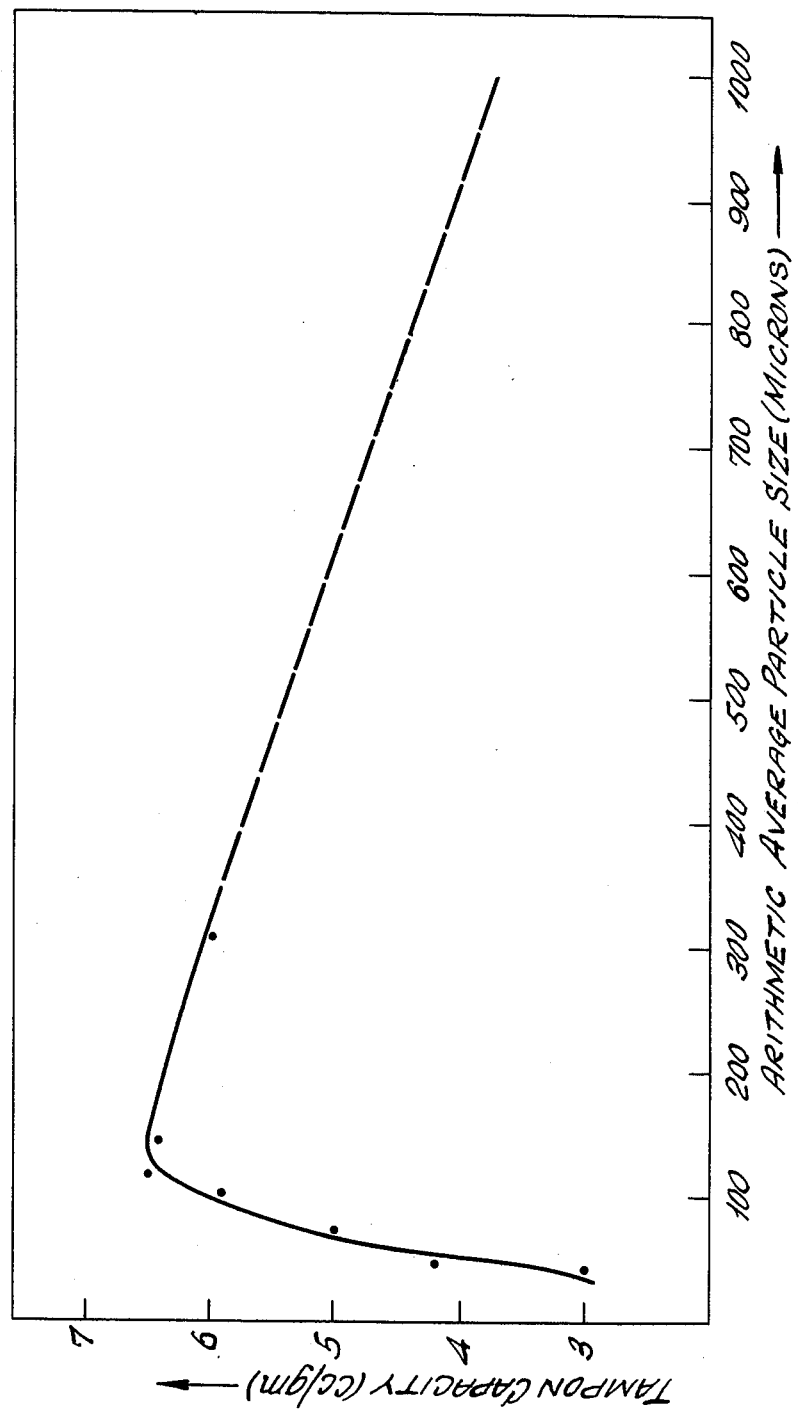

POWDERED GRAFTED CELLULOSE

This application is a continuation-in-part of my copending application Ser. No. 531,149, filed on Dec. 9, 1974 now abandoned.

BACKGROUND OF THE INVENTION

This invention relates to absorbent bodies as used in products designed to absorb body exudates such as catamenial napkins and tampons, diapers, surgical sponges, wound dressings and the like. These products generally comprise an absorbent body enveloped by a material, at least a portion of which is permeable to body exudates. In the case of catamenial tampons, for example, the absorbent body is generally in a highly compressed form and in some circumstances may be used without the enveloping material. In the case of diapers and sanitary napkins, the absorbent body is generally in the form of a pad sandwiched between a facing sheet and a backing sheet, the latter of which may be impermeable to body exudates. Notwithstanding the particular configuration, it is, of course, desirable that the absorbent body have a relatively high absorbency per unit weight for the aqueous based body exudate fluids.

Most commonly, absorbent bodies for these products are made of highly porous batts of wood pulp fiber and generally meet the criteria for products of this nature in that wood pulp is absorbent, inexpensive and, in the form of loose batts, comfortable to the ultimate user. Nevertheless, in efforts to improve these absorbent products, the art is now replete with modifications of, and substitute materials for, wood pulp.

One such modified material is disclosed in U.S. Pat. No. 3,256,372 and is described therein as a product produced by chemically grafting, in a water slurry, hydrophilic polymer chains onto cellulose fibers such as wood pulp (this product, among others, hereinafter referred to as grafted cellulose). The wet fibers obtained from the slurry are then extruded into shaped porous articles and carefully dried to maintain their porous structure by such special techniques as freeze-drying or solvent drying. The resultant product is highly absorbent and is useful in such products as cigarette filters. Unfortunately, however, the extruded shapes are relatively hard, brittle and, when incorporated into a product such as a disposable diaper or a catamenial device, can cause discomfort to the user.

SUMMARY OF THE INVENTION

It has now been discovered that highly absorbent grafted cellulose may be effectively incorporated within an absorbent body and without the drawbacks heretofore encountered. This is accomplished by first comminuting the grafted cellulose into the form of powders while carefully controlling the arithmetic average particle size. The powders may then be dispersed throughout the absorbent body but preferably are provided as a core or central layer or layers within the absorbent body, the remainder of which is conventional absorbent material.

Specifically, in accordance with this invention, an absorbent body is provided with cellulose particles having grafted thereon hydrophilic chains of carboxyl-, carboxylate-, and/or carbamide-bearing moieties, said particles having a selected arithmetic average particle size of about 50 to about 1000 microns. Preferably, the particles are about 70 to about 500 microns in size, and still more preferably 100 to 350 microns. The remainder of the absorbent body may be any of the commonly used absorbent materials such as, for example, wood pulp, rayon, tissue wadding, absorbent foam, etc.

In one aspect of the invention, the grafted cellulose particles are distributed throughout the absorbent body and in this manner, exhibit superior absorption properties. In a preferred embodiment, however, the grafted cellulose particles are disposed as a central core or layer within an absorbent body, the remainder of which is conventional absorbent materials. For example, when the absorbent body is used as a sanitary napkin or diaper, the grafted cellulose particles are advantageously provided as a central layer sandwiched between wood pulp layers or wadded tissue layers. In the case of a cylindrical tampon, the particles may be disposed therein as one or more central cores. Again, when used in tampons of the type made by first winding a rectangular pad into a cylinder and then compressing the same, the particles may be layered or sprinkled onto the surface of the pad, and then wound with the pad prior to compressing. When used in this manner, the core of particles assumes a spiral configuration in radial cross-section and is therefore well distributed within the finished tampon.

When the grafted cellulose is presented in an absorbent body in any of the above-described forms, the problems of user discomfort are entirely obviated and, when the size of the particles is controlled as herein described, the absorbency of the body is greatly increased. A highly significant added advantage to the use of grafted cellulose in this powdered form is that there is no longer a need to preserve the structural stability of the products being dried from the grafting slurry in which they are made and accordingly the expensive exotic drying methods such as freeze drying and solvent drying, heretofore taught by the prior art as essential in the production of absorbent grafted cellulose, may now be dispensed with and conventional air drying or oven drying techniques will produce highly usable products at a greatly reduced cost.

As used herein and in the appended claims, the term "powder" is taken to mean a non-fibrous substance in the form of fine discrete particles which cannot be formed into a fabric web. Usually, the length, width and thickness dimensions of the particles are within two orders of magnitude, or less, of each other. The powder particles can have various shapes such as spherical, rounded, angular, acicular, irregular, fragmented, or the like.

The term "fiber" as used herein and in the appended claims is taken to mean a unit of matter characterized by having a length at least two orders of magnitudes greater than its diameter or width and which can be formed into a fabric web.

The term "arithmetic average particle size" as used herein and in the appended claims is taken to mean particle size calculated from the expression:

$$\Sigma\ ab/100 = \text{arithmetic avg. particle size}$$

where "$a$" is weight fraction of particles expressed as percentage of total weight and "$b$" is the average particle size for "$a$" expressed in microns, a method of measuring these values being described herein.

BRIEF DESCRIPTION OF THE DRAWINGS

In the drawings:

FIG. 1 is a perspective view of an absorbent dressing or a disposable diaper embodying this invention, a portion thereof being broken away to show interior detail;

FIG. 2 is a cross-sectional view of the dressing or diaper of FIG. 1 taken along line 2—2;

FIG. 3 is a perspective view of a partially rolled blank for compressing into a first catamenial tampon embodying this invention;

FIG. 4 is a perspective view of a finished tampon made from the blank of FIG. 3, a portion thereof being broken away to show interior detail;

FIG. 5 is a perspective view of a partially folded blank for compressing into a second catamenial tampon embodying this invention;

FIG. 6 is a cross-sectional view of the finished tampon made from the blank of FIG. 5 taken through an axial plane through the tampon;

FIG. 7 is a perspective view of a catamenial sanitary napkin embodying this invention, a portion thereof being broken away to show interior detail;

FIG. 8 is a cross-sectional view of the sanitary napkin of FIG. 7 taken along line 8—8; and FIG. 9 is a graphical representation showing the relationship between arithmetic average particle size of the grafted cellulose of this invention and the absorbency of tampons made therewith.

DESCRIPTION OF THE PREFERRED EMBODIMENTS

The Grafted Cellulose

A wide variety of cellulosic fibers can be utilized as starting materials for producing the grafted cellulose suitable for the present invention. Typically, such fibers are: cotton, cotton linters, wood pulp, bagasse pulp, jute, rayon, and the like. The cellulosic fibers are then modified by grafting thereon a hydrophilic chain of the general formula:

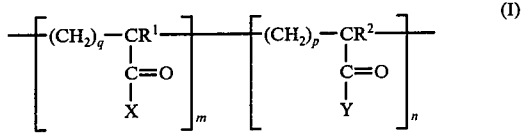

(I)

wherein $R^1$ and $R^2$ are selected from the group consisting of hydrogen and alkyl having 1 to 4 carbon atoms, X and Y are selected from the group consisting of —OH, —O(alkali metal), and —NH$_2$, wherein $m$ is an integer having a value of 0 to about 5000, $n$ is an integer having a value of 0 to about 5000, the total number of $m$ and $n$ moiety on a chain is at least 500, $p$ is an integer having a value of zero or 1, and $q$ is an integer having a value of 1 to 4.

Preferred hydrophilic chains are those selected from the group consisting of polyacrylic acid, alkali polyacrylate such as sodium or potassium polyacrylate and copolymers of these which may be obtained, for example, by the hydrolysis of polyacrylonitrile chains. It should be understood that in the hydrolysis of polyacrylonitrile chains, some polyacrylamide, an intermediate product is formed, and may be also present in the final product.

While the detailed mechanism by which the grafting of the hydrophilic chain or chains onto a cellulosic backbone is not fully known, it is believed that one possibility is that grafting takes place through a free radical mechanism whereby the free radical is situated on the cellulosic backbone which serves as a reducing agent and the hydrophilic chain is attached to the cellulosic reducing agent through a carbon linkage to produce a graft copolymer of the type:

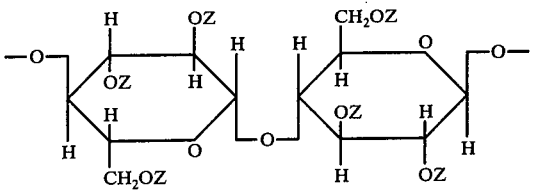

wherein Z represents the hydrophilic chain of Formula I above.

The foregoing hydrophilic chains are polymers of an olefinically unsaturated carboxylic acid or a derivative thereof with itself or with at least one other monomer copolymerizable therewith. The resulting polycarboxylic acid-type polymers can, for example, include those containing monomer units such as acrylic acid, acrylic anhydride, methacrylic acid, crotonic acid, maleic acid, itaconic acid, citraconic acid, alpha-dimethyl maleic acid, alpha-butyl maleic acid, fumaric acid, aconitic acid, as well as partial salts, amides and esters thereof. Anhydrides of any of the aforesaid acids can also be employed.

The initial copolymers of anhydrides with another monomer can be converted to carboxyl-containing copolymers by reaction with water, and carboxylate-containing moieties, such as ammonium or alkali salts thereof, by reaction with aqueous solutions of alkali metal compounds such as sodium hydroxide, potassium hydroxide, and the like or with aqueous ammonia.

The copolymers are formed in a known manner by reacting admixtures of the desired monomers in the presence of a peroxide catalyst in a suitable solvent for the monomers.

The obtained copolymers are conveniently identified in terms of their monomeric constituents. However, the names so applied to the copolymers refer to the molecular structure of the polymer and are not limited to the polymers prepared by the copolymerization of the specific monomers. In many instances, the identical copolymers may be prepared from other monomers and converted to the desired copolymer by a subsequent chemical reaction.

A preferred hydrophilic polymer chain can be prepared by several methods known in the art. Illustrative of such methods are the following:

(1) Polymerize acrylonitrile and hydrolyze with an alkaline solution to form alkali salts of polyacrylic acid.

(2) Polymerize acrylic acid or alkali salts of acrylic acid.

(3) Polymerize methacrylonitrile and hydrolyze with acids to form polymethacrylic acid or hydrolyze with an alkaline solution to form alkali salts of polymethacrylic acid.

(4) Polymerize methacrylic acid or alkali salts of methacrylic acid.

(5) Polymerize acrylamide, optionally followed by hydrolysis.

(6) Polymerize methacrylamide, optionally followed by hydrolysis.

(7) Form copolymers of any of the above monomers.

Methods of graft-copolymerizing olefinically-unsaturated chains onto cellulose are known in the art. Thus, grafting of the hydrophilic material onto cellulose can be accomplished simultaneously with the formation of the hydrophilic polymeric material in an aqueous medium, because the peroxide catalyst used to copolymerize the various monomers forms a redox catalyst system in combination with a reducing agent and thus also serves to effect chain transfer onto the cellulose. Suitable reducing agents for this purpose are ceric ion, ferrous ion, cobaltic ion, $(NH_4)_2S_2O_8$, cuprous ion, and the like. The desired ions can be supplied in the form of salts such as ceric ammonium nitrate, ferrous ammonium sulfate, and the like. Graft-copolymerization of olefinically-unsaturated chains can also be effected by irradiation (ultraviolet-, gamma- or X-radiation) or by heating in an aqueous medium in the presence of an emulsifier.

Cellulose fibers or pulp can be slurried in water containing a graft-copolymerization catalyst system and the monomer or monomers added to the slurry and polymerized in situ at ambient temperature or above depending on the catalyst employed. In this manner a portion of the formed hydrophilic polymer may also be physically entrapped into the cellulosic material during the polymerization process. The preparation of suitable starting materials for practicing the present invention is also illustrated in U.S. Pat. No. 3,256,372.

Hydrophilic chain loading on cellulose can vary from about 10 percent by weight to about 90 percent by weight, and preferably is about 40 to about 80 percent by weight of the grafted cellulose.

The Comminuted Grafted Cellulose

The grafted cellulose produced in the aforedescribed manner may be dried at atmospheric pressure and in a gaseous atmosphere so as to drive off the water and to produce a relatively dense, non-porous, stiff, brittle and hornified material. In accordance with this invention, the hornified material is then comminuted into a powder having an arithmetic average particle size of about 50 to about 1000 microns, preferably about 70 to about 500 microns and still more preferably about 100 to 350 microns. This particle size range will exhibit surprisingly high absorbent capacity when incorporated into absorbent bodies.

The comminution can be effected in any convenient manner, for example, by grinding in a ball mill or by utilizing other size reduction equipment such as a micropulverizer, a Wiley mill, a Weber mill or the like. While the relationship between the particles' size and their absorbing properties is not entirely understood, it is believed to relate to the tendency for these particles, when wetted with aqueous based fluids, such as those exuded from the body, to gel at their surfaces, the gelling then preventing moisture from penetrating further into the mass. When small particles are used, particularly in a mass of small particles, the particles on the outside of the mass, first contacted with liquid, gel and, owing to their close packing, tend to form an occlusive film around the interior particles precluding further penetration of fluid into the mass and resulting in less efficient utilization of the absorbent properties of the powder. On the other hand, when larger particles are used in a mass of such particles, fluid can penetrate into the spaces between particles and will wet substantially all of the particles in the mass. As the size of the particles are increased, however, the ratio of that portion of each particle which is wetted with fluid to that central portion of the particle from which fluid is excluded because of the gelling effect decreases and accordingly, again there is less efficient use of the mass of absorbent material.

Incorporation of Grafted Cellulose in Absorbent Bodies

Referring now to the drawings, in FIGS. 1 and 2, an absorbent dressing or disposable diaper 10 is provided with a porous facing sheet 11 which can be, for example, gauze, tissue or a nonwoven fabric. A moisture-impermeable backing sheet 12 is provided preferably made of a thin-gauge polyolefin or polyester sheet such as a polyethylene or polyethylene terephthalate film. It will be understood by one skilled in the art that the impermeable backing sheet is used where a dry surface is required such as in a diaper or dressing. In circumstances where this is not necessary, such as in a surgical sponge, the backing sheet may be of a permeable material such as, for example, the same material as the facing sheet. The facing and backing sheets are adhered together along common edges 13 with a suitable, preferably water-insoluble, adhesive or may alternatively be heat-sealed if thermoplastic materials are used in the sealing area. Sandwiched between the facing sheet 11 and the backing sheet 12 is an absorbent body 14 in the form of a planar pad made of absorbent fibers 15 such as cellulosic fibers, e.g., wood pulp, rayon or the like. In accordance with this invention dispersed throughout this absorbent layer 14 are particles 16 of the highly absorbent grafted cellulose of this invention which may be, for example, cellulose having hydrophilic chains such as polyacrylamide-sodium polyacrylate copolymer chains, polyacrylic acid-sodium polyacrylate copolymer chains, or the like. The grafted cellulose particles are comminuted to an arithmetic average particle size of from 50 to 1000 microns, for example 110 microns, and the resulting absorbent body 14 then has a capacity for absorbing body fluids which greatly exceeds a body of equal weight composed entirely of wood pulp.

The incorporation of the grafted cellulose into absorbent body 14 in the manner shown in FIGS. 1 and 2, i.e., distributed throughout the body, is highly effective but is difficult to accomplish in high speed manufacturing processes in that the small grafted cellulose particles are not easily distributed uniformly throughout the fibrous mass of wood pulp and instead tend to settle in large clumps which would tend to gel upon being wetted with body fluid. This problem becomes particularly acute in the manufacture of catamenial tampons which undergo several processing steps before the final product is completed. A particularly satisfactory solution to this problem is illustrated in the embodiment of this invention shown in FIGS. 3 and 4 of the drawings. Shown in FIG. 3 is an elongated pad 18 of absorbent material such as rayon fibers having a generally rectangular shape and illustrated as formed into a cylinder by rolling from one end to the other in a direction parallel to the longitudinal sides of the pad. In accordance with this aspect of the invention, prior to rolling, a thin layer 20 of the grafted cellulose material is applied to the surface of the rectangular pad so that upon rolling, the layer forms strata 22 of the grafted cellulose alternating with the rayon, as viewed in the radial cross-section. The rolled pad is then compressed in a die to the desired tampon shape 24 as is illustrated in FIG. 4. The tampon is provided with the usual withdrawal string 26 which may be sewn through the removal end of the tampon or applied by other means known in the art, such as being looped or tied around the rectangular pad 18 prior to rolling. The grafted cellulose strata 22 in the finished product are held tightly in place by the compressed rayon and because each stratum, comprising particles of the size prescribed herein, is separated by a layer of rayon, the gelling problem is substantially obviated and an excellent absorbent tampon results which additionally is relatively simple to manufacture on high speed equipment.

FIGS. 5 and 6 illustrate another embodiment of this invention in a catamenial tampon. A rectangular pad 27 of wood pulp laid upon a porous nonwoven cellulosic fabric cover 25 has a layer 28 of the herein prescribed grafted cellulose applied to one surface. The pad 27 with the nonwoven cover 25 is then folded about its longitudinal center and folded once more into a U-shaped blank, as illustrated in FIG. 5. The blank is then placed in a cylindrical die and compressed radially and/or longitudinally into the desired tampon shape 30 as shown in FIG. 6. A withdrawal string 34 is provided at the withdrawal end of the compressed tampon 30 and may be attached in a manner similar to that described above, i.e., sewn on, looped or tied around the pad 27 prior to folding, etc. The finished tampon 30 will then comprise centrally located strata or cores of grafted cellulose 32 surrounded and held in place by compressed layers of wood pulp 36 which in turn are held in place by the nonwoven cover. When the particles are of the size and nature herein prescribed, the tampon will be substantially more absorbent than one of similar construction and weight composed entirely of wood pulp. In addition to the simple structure of this tampon, an added advantage is that the most absorbent material, the cores 32 of grafted cellulose, are within the tampon thus creating a positive driving force for liquid absorption directed toward the interior. Accordingly, the tampon tends to collect absorbed liquid in the cores, leaving the outer layer relatively dry, thereby decreasing the likelihood of surface puddling or expulsion of fluid under the occasional stresses placed on the tampon when worn.

FIGS. 7 and 8 illustrate the invention embodied in a sanitary napkin 37. An absorbent pad 38 comprised of, for example, wood pulp is enveloped by a liquid permeable wrapper 40 which extends at both ends beyond the pad so as to provide attachment tabs 42 and 44. A liquid impermeable sheet 46 is sandwiched, on one surface of the pad, between the pad and the wrapper and may extend, at least partially over the sides of the pad. The impermeable sheet may be for example, a polyethylene film. In a central portion of the pad 38, there is interposed, a layer 48 of the herein prescribed grafted cellulose.

It will be appreciated by one skilled in the art that the methods of incorporating the grafted cellulose particles of this invention into the specific absorbent bodies are to a large measure interchangeable and for example, the dressing or diaper of FIGS. 1 and 2 may be provided with a central core such as for the sanitary napkin of FIGS. 7 and 8. Likewise, the tampons of FIGS. 3-6, as well as the napkin of FIGS. 7 and 8, may have the grafted cellulose distributed throughout their respective absorbent bodies, as is shown for the dressing or diaper of FIGS. 1 and 2.

The relative quantities of grafted cellulose which may be incorporated into the absorbent bodies of this invention may vary widely depending upon the properties desired for the finished product. An increase in the quantity of grafted cellulose will generally produce a more absorbent product but will also increase the difficulty of manufacturing the same and will certainly increase the cost of the product. In general, for the products described herein, it is desirable to incorporate from about 1 to about 70 percent by weight of grafted cellulose, based on the total weight of the absorbent body and preferably about 5 to about 50 percent.

The invention will be more fully understood from a consideration of the following examples wherein grafted cellulose is incorporated into various absorbent bodies. The grafted cellulose is a copolymer of cellulose and hydrophilic chains, said chains having the structure:

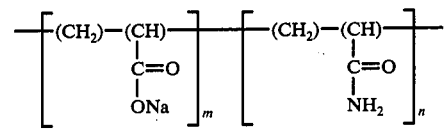

and accounting for approximately 50% by weight of the grafted cellulose with the $n$ moities accounting for less than 5% by weight of structure.

As used in these examples, the arithmetic average particle size for a mass of absorbent material is determined by using a pulse type Sonic Sifter manufactured by the Allan-Bradley Company of Milwaukee, Wis. and designated by them as Model L3P. The sifter is provided with a series of vertically arranged screens for passing particles of 500, 420, 355, 250, 125, 90, 63, 38 and 20 microns respectively. A 1 gram sample of the material tested is run for 10 minutes at a sift amplitude of 6 and a pulse amplitude of 3. The weight, as a percentage of the 1 gram sample, remaining on each screen after ten minutes is determined and reported as "$a$." The arithmetic average of that screen size and the screen size immediately above it is reported as "$b$" (except for the topmost screen wherein "$b$" is simply this screen size). The arithmetic average particle size is then calculated as:

$\Sigma \, ab/100$ the summation being taken for all of the screens.

EXAMPLE I

Tampons, of the type shown in FIGS. 5 and 6 of the drawings are prepared using central cores of the above described grafted cellulose of varying arithmetic average particle size as shown in the following Table 1. Each tampon has a density of about 0.4 gm/cc, a diameter of about 0.57 inches and an axial length of about 1.68 inches and has a nonwoven cover as is described in connection with FIG. 6. The central cores of grafted cellulose account for 50% of the weight of the tampon, the remainder being Southern pine, kraft, fully bleached wood pulp fibers which are comminuted in a hammer mill to an arithmetic average particle size of 1500 microns. A control tampon having the same specifications as the above with the exception that it consists of 100% of the wood pulp, is also prepared. The capacity of each of these tampons to absorb a 1% by weight aqueous sodium chloride solution under simulated in-use conditions is determined by submerging one end of the tampon in the solution for a period of 20 minutes while maintaining the sides of the tampon under a confining pressure of 24 inches of water, said confining pressure maintained by enveloping the tampon in a hydraulically inflated polyethylene sleeve. The tampon is maintained submerged until fluid appears on the non-submerged end of the tampon at which time free solution is drained from the system while maintaining confining pressure. The pressure is then released and the weight of solution absorbed by the tampon is reported in Table 1 as the tampon capacity in units of volume of fluid absorbed per unit weight of tampon and graphically represented in FIG. 9.

TABLE 1

Absorbency of Grafted Cellulose Powder/Pulp Tampons: Effect on Particle size

| Sample | Wood Pulp Wt. % | Wood Pulp Size[1] | Grafted Cellulose Wt. % | Grafted Cellulose Size[1] | Tampon Capacity (cc/g) |
|---|---|---|---|---|---|
| 1 | 100 | 1500 | 0 | — | 2.7 |
| 2 | 50 | 1500 | 50 | 311 | 6.0 |
| 3 | 50 | 1500 | 50 | 145 | 6.4 |
| 4 | 50 | 1500 | 50 | 117 | 6.5 |
| 5 | 50 | 1500 | 50 | 102 | 5.9 |
| 6 | 50 | 1500 | 50 | 71 | 5.0 |
| 7 | 50 | 1500 | 50 | 49 | 4.2 |
| 8 | 50 | 1500 | 50 | 43 | 3.0 |

It is evident from the data that particle size has a significant effect on absorbency. Maximum absorption is obtained with the grafted cellulose having an arithmetic average particle size of 117 microns. In the range of about 50 microns to an extrapolated value of 1000 microns, the capacity of the tampons are greatly improved over that of the 100% wood pulp tampon. An examination of the tampons having grafted cellulose particles in the range of about 70 microns indicates that a portion of the grafted material is not fully saturated with liquid and, at a particle size of about 40 microns, the capacity of the tampon is essentially the same as the wood pulp control tampon.

EXAMPLE II

Tampon samples are prepared as in the above example with the exception that three denier, rayon staple fibers are substituted for the wood pulp. The central core is the grafted cellulose particles having an arithmetic average particle size of 145 microns and accounting for 50% of the total weight of the tampon.

A tampon consisting of 100% rayon is also prepared. The capacity of the tampons is tested, as in the preceding example with the result that the 100% rayon tampon has a capacity of 3.1 cc/gm as compared to the rayon/-grafted cellulose tampon of this invention which has a capacity of 6.4 cc/gm.

EXAMPLE III

Two sanitary napkins are prepared having the construction of FIGS. 7 and 8 with the exception that the first napkin has an absorbent pad consisting of 100% Southern pine, bleached, kraft, comminuted wood pulp. In the second napkin, 15% of the wood pulp is removed from the center of the pad and replaced with an equal weight of the grafted cellulose material having an average particle size of 145 microns. The two napkins are tested for absorbency using the Burette Drip Test, wherein, the napkin to be tested is placed on a glass plate resting on a ring stand and a 50 ml burette is positioned two inches above the napkin so as to release liquid dropwise onto the center of that face of the napkin normally worn against the body. A mirror is placed below the glass plate to allow observation of the opposite face. The quantity of liquid released upon the napkin from the burette at the time that napkin failure is observed (i.e., when liquid is first observed on the bottom or sides of the napkin cover), is recorded as the Absorbency.

For this example, a 1% aqueous sodium chloride solution was allowed to fall dropwise at a rate of 4 cc/min. The test on the 100% wood pulp napkin resulted in an Absorbency of 26 cc. of liquid at failure. In marked contrast thereto, the test on napkin containing the grafted cellulose of this invention resulted in an Absorbency of 55 cc.

EXAMPLE IV

Small dressings having planar dimensions of 6.25 × 2 inches, weighing 3.6 gms and of the kind illustrated in FIGS. 1 and 2 are prepared wherein various quantities of the grafted cellulose pulp having an arithmetic average particle size of 145 microns are layered between Southern pine, kraft, bleached wood pulp layers. The dressings are tested using the Burette Drip Test method as described above with a 1% sodium chloride solution at a rate of 0.4 cc/min. The results are reported below in Table 2. It will be noted that even a quantity as low as 5% by weight of the grafted cellulose based on the total dressing weight produced a marked improvement in Absorbency over that containing only wood pulp.

TABLE 2

Absorbency of Grafted Cellulose Powder/Pulp Pads

| Weight % Grafted Cellulose (Based on total dressing weight) | Absorbency (cc) |
|---|---|
| 0 | 2.3 |
| 5 | 3.5 |
| 10 | 6.7 |

What is claimed is:

1. An absorbent body comprising cellulose particles having grafted thereon hydrophilic chains of the general formula:

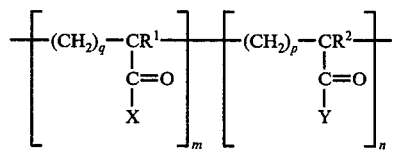

wherein $R^1$ and $R^2$ are selected from the group consisting of hydrogen and alkyl having 1 to 4 carbon atoms, X and Y are selected from the group consisting of —OH, —O(alkali metal), and —NH$_2$, wherein $m$ is an integer having a value of 0 to about 5000, $n$ is an integer having a value of 0 to about 5000, the sum of all $m$ and $n$ groups is at least 500, $p$ is an integer having a value of 0 to 1, and $q$ is an integer having a value of 1 to 4; the individual particles of said grafted cellulose having an arithmetic average size of about 70 to about 500 microns; said grafted cellulose comprising from about 5 to about 50% by weight based on the weight of the absorbent body.

2. The absorbent body of claim 1 wherein the hydrophilic chains are selected from the group consisting of polyacrylic acid, alkali polyacrylate, polyacrylamide and copolymers of these.

3. The absorbent body of claim 2 wherein the hydrophilic chains comprise alkali polyacrylate.

4. The absorbent body of claim 2 wherein the hydrophilic chains are copolymers of polyacrylamide and sodium polyacrylate.

5. A catamenial device comprising an absorbent body of cellulose fibers and cellulose particles having grafted thereon hydrophilic chains of the general formula:

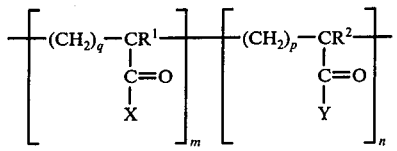

where $R^1$ and $R^2$ are selected from the group consisting of hydrogen and alkyl having 1 to 4 carbon atoms, X and Y are selected from the group consisting of —OH, —O(alkali metal), and —NH$_2$, wherein $m$ is an integer having a value of 0 to about 5000, $n$ is an integer having a value of 0 to about 5000, the sum of all $m$ and $n$ groups is at least 500, $p$ is an integer having a value of zero to 1, and $q$ is an integer having a value of 1 to 4; the individual particles of said grafted cellulose having an arithmetic average size of about 70 to about 500 microns; said grafted cellulose comprising from about 5 to about 50% by weight based on the weight of the absorbent body.

6. The device of claim 5 wherein said grafted cellulose particles are substantially uniformly distributed in the absorbent body.

7. The device of claim 6 wherein said grafted cellulose particles comprise at least one core within said absorbent body.

8. The device of claim 7 wherein said absorbent body comprises a plurality of cores comprised of said grafted cellulose particles, said cores being separated by a plurality of compressed cellulose fibers.

9. A tampon comprising the device of claim 8 wherein said absorbent body comprises a pad of said cellulose fibers having a layer of said grafted cellulose particles thereon, said pad being rolled into cylindrical form and compressed into the final tampon shape.

10. A tampon comprising the device of claim 8 wherein said absorbent body comprises a pad of said cellulosic fibers having a layer of said grafted cellulose particles thereon, said pad being folded upon itself to contain said particles and said folded pad being compressed into the final tampon shape.

11. A sanitary napkin comprising the device of claim 5 wherein said absorbent body is in the form of a planar pad sandwiched between a backing sheet and a facing sheet, at least one of which is fluid permeable.

12. The napkin of claim 11 wherein the backing sheet is fluid permeable.

13. The napkin of claim 12 wherein said backing sheet and said facing sheet are formed from a continuous cover sheet enveloping the absorbent body.

* * * * *

UNITED STATES PATENT AND TRADEMARK OFFICE
CERTIFICATE OF CORRECTION

PATENT NO. : 4,105,033
DATED : August 8, 1978
INVENTOR(S) : Pronoy Kumar Chatterjee et al.

It is certified that error appears in the above-identified patent and that said Letters Patent are hereby corrected as shown below:

In Column 9, line 24, Table I, a footnote should read

1) Arithmetic Average Particle Size, Microns

Signed and Sealed this

Fifth Day of June 1979

[SEAL]

Attest:

RUTH C. MASON
*Attesting Officer*

DONALD W. BANNER
*Commissioner of Patents and Trademarks*